000

United States Patent [19]

Codignola et al.

[11] 4,288,641

[45] Sep. 8, 1981

[54] PROCESS FOR THE PREPARATION OF 1,4-BUTYNEDIOL AND RELATED CATALYST

[75] Inventors: Franco Codignola, Castenedolo; Giorgio Vergini, Milan; Paolo Gronchi, Milan; Paolo Centola, Milan, all of Italy

[73] Assignee: Societa Italiana Serie Acetica Sintetica S.p.A., Milan, Italy

[21] Appl. No.: 85,792

[22] Filed: Oct. 17, 1979

[30] Foreign Application Priority Data

Jun. 15, 1979 [IT] Italy ................................ 23655 A/79

[51] Int. Cl.³ ............................................ C07C 33/046
[52] U.S. Cl. ..................................... 568/855; 252/454
[58] Field of Search .......................................... 568/855

[56] References Cited

U.S. PATENT DOCUMENTS 3,352,924 11/1967 Gladrow et al. ..................... 568/883

OTHER PUBLICATIONS

Reppe et al., "Alien Property Custodian", Ser. No. 327,820, published Apr. 20, 1943.

Primary Examiner—Joseph E. Evans
Attorney, Agent, or Firm—Cushman, Darby & Cushman

[57] ABSTRACT

The process for the preparation of 1,4-butynediol through the reaction of acetylene with formaldehyde in the presence of a catalytic metal, preferably copper, is improved by using, as the support of the catalytic metal, a molecular sieve or synthetic zeolite to which the catalytic metal is chemically bonded through an ion exchange reaction.

There are obtained increased production rates and selectivity and the polymer of acetylene, namely cuprene, is essentially prevented from being formed.

3 Claims, No Drawings

PROCESS FOR THE PREPARATION OF 1,4-BUTYNEDIOL AND RELATED CATALYST

The present invention relates to a process for the preparation of 1,4-butynediol as well as to the related catalyst.

According to the known reaction for the production of 1,4-butynediol acetylene and formaldehyde are reacted in the presence of metal copper as the catalyst, the metal forming with acetylene copper acetylide.

This process has been described for the first time in the U.S. Pat. No. 2,232,867 to Reppe et al, it being known under their name and, a-part from secondary modifications, is the process still used for this production.

However this process is affected with some problems and disadvantages which can be shortly resumed as follows:

(a) the reaction conditions involve the reaction of acetylene and formaldehyde under an acetylene pressure of about 5 to 7 atmospheres and at a temperature of about 90° to 120° C.

Under these reaction conditions the dangerous limits of explosive decomposition of the acetylene are overcome with the self-evident risks and problems.

(b) by using the known catalyst, consisting of metal copper supported onto an amorphous matrix (silica, alumina, carbon, pumice and other materials), of the a polymer of acetylene is formed, known under the name of cuprene by which the surface of the catalyst is coated (the catalyst being thus made inactive), and the catalyst bed becomes clogged, whereby the process must be stopped in order to restore the catalytic bed and the suitable flow conditions of the reaction mixture through the catalyst.

(c) As already mentioned, the catalyst is in fact a metal acetylide which, due to its dangerousness, is never used at the pure state, but is formed on the catalytic metal, usually monovalent copper, which in turn is supported onto an inorganic amorphous matrix, of the above mentioned type, or onto carbon, normally in powder form.

In this type of support the metal atoms are finely and irregularly dispersed, a heterogeneous mass being thus formed, comprising the supporting particles and the metal particles, without any chemical hand between each other. Thus, not only the metal copper is only partially used as regards the forming of the acetylide and the true catalytic action, but the forming of cuprene is promoted; the latter disadvantage is very likely attributable to the exceedingly high closeness (statistically probable) of the catalytic copper atoms, the polymerization reaction of the acetylene and thus the forming of the undesired product being consequently enhanced.

As a matter of fact this situation is due to the fact that in the known catalysts the support is impregnated with a cupric solution, whereas the subsequent calcination causes oxides of bivalent copper to be formed, the reduction to monovalent copper taking only place during the first phase of the reaction, in hot conditions, in the presence of formaldehyde and acetylene, with the forming of the copper acetylide.

The latter has an amorphous polymeric structure, comprising a high number of acetylene molecules and of copper atoms, with a molar ratio between acetylene and copper not less than 2.

The consequence is that only a small proportion of copper is present at the surface and thus available for the catalytic activity (with the evident reduction of yield) and, on the contrary, the polymerization of acetylene to cuprene is promoted.

As regards the yields of this process, they are not higher than 1 kg of 1,4-butynediol per liter of 12% Cu catalyst per day, and the catalyst selectivity is not higher than 95%. The main purpose of the present invention is that of providing a process for the production of 1,4-butynediol by reacting acetylene and formaldehyde, in which not only the yield and the selectivity are increased, but the forming of cuprene is essentially eliminated and the process taken place under safety conditions as regards the risks of explosive decomposition of the acetylene.

Such a purpose is attained with a process for the preparation of 1,4-butynediol, of the type in which acetylene and formaldehyde are reacted at a temperature of between 70° C. and 150° C., in the presence of a catalytic metal, preferably copper, capable of forming acetylides with the a cetylene under the reaction conditions, characterized in that a catalyst is used comprising an inorganic support selected in the class of the molecular sieves or synthetic zeolites, chemically bonded to the catalytic metal whereby the metal atoms and the support form only the inorganic, polymeric, crystal lattice, in which the metal atoms are positioned at regularly distributed sites, with mutual spacing well defined and capable of regulation within wide limits.

Another object of the present invention are as well the novel catalyst, particularly useful for the reaction between acetylene and formaldehyde for the preparation of 1,4-butynediol, resulting from an ion exchange between a synthetic zeolite or molecular sieve and the catalytic metal, said ion exchange being controlled to a desired percentage of the catalytic metal, the resulting catalyst being lastly a silicon-aluminate of the catalytic metal and possibly of another cation as a function of the percentage of exchanges catalytic metal.

Since the ion exchange operations between the catalytic metal, for instance in form of a solution of a salt thereof, and the zeolite are well known in the art, it seems not necessary to further discuss them, whereas it is worth to point out that, since molecular sieves are crystalline materials which, besides a high surface area, have also a precise and determined porosity, characterized by internal cavities, having regular shape, size, geometrical characteristics and distribution, also the catalytic material resulting from the ion exchange has the same physico-chemical and structural properties: consequently, when the catalyst come into contact with acetylene in the reaction environment, gives place to the acetylides corresponding to the catalytic metal, with consequent activation of the acetylene for the reaction with the carbonyl compound (aldehyde or ketone) and essential inhibition of the cuprene production. As it will be confirmed by the following examples, having only illustrative but non limitative purpose, thanks to the process and to the catalyst of the present invention, both the yield of the desired product and the selectivity of the reaction are increased in an unexpected manner.

Particularly, by carrying out the reaction at a temperature of between 80° C. and 110° C. and under pressures of, between 0.5 and 1.5 atmospheres, and by using formaldehyde in aqueous solution at a concentration varying between 5 and 40% and acetylene fed from a gas cylinder and suitably purified, there have been obtained production rates up to 1.6 kg of 1,4-butynediol per liter of catalyst and per day in the case of a reactor with fixed bed of catalyst, and production rates up to 4,8 to 6 kg of 1,4-butynediol per liter of catalyst and per day in the case of a fluid bed of catalyst; on the contrary, in the case of the, Reppe process the production rates given in the literature are of about 1 kg of 1,4-butynediol per day and liter of catalyst containing 12% copper.

It is to be noted that the above results are achieved with the catalyst of the present invention which, furthermore, contains remarkably lower percentages of catalytic metal, whereby the production rates, if referred to the latter, are still higher.

Another important feature of the invention resides in that the afore said results are obtained by operating at feeding pressures of acetylene definitely lower than the limit of explosive decomposition of the acetylene under the thermal conditions of the reaction.

Lastly in the experiments above referred to it has been noted that, after more than 250 hours operation of the catalyst not only the catalyst activity was unchanged, but also no trace, even minimum, of cuprene was detected.

As regards the reaction by-products, the production of propargyl alcohol is higly controlled, with concentrations of between 1% and 2% (maximun) of the reaction mixture.

EXAMPLE 1

A stainless steel autoclave, having stirring means and a capacity of 500 mls, electrically heated and having a thermometric well, an inlet and an outlet for gases and (or liquids) is charged with 300 mls of a water solution of formaldehyde (37.5% by weight) together with 151 mls (128 g) of the catalyst formed by 13×sodium zeolite ion exchanged up to 2.77% by weight of Copper.

After several purging operation with nitrogen and vacuum, under cold conditions, both the stirring means and the heating system are switched on.

When the operating themperature of 90° C. is attained, the feeding of acetylene is started, it being taken from a gas cylinder and suitably purified, until the pressure is 1.5 atmospheres, leaving the gas freely flowing into the reactor.

Small samples of liquid are periodically taken for the chemical and chromatographic analyses of the reactants and of the products.

The following results were obtained:
(A) after 8 hours of reaction:
formaldehyde: 25.1%
1,4-butynediol: 14.0%
propargyl alcohol 1.29%
(B) after 16 hours of reaction:
formaldehyde: 19.8%
1,4-butynediol: 21.0%
propargyl alcohol: 1.76%

The production rate of the catalyst is 800 of 1,4-butynediol per liter of catalyst and per day. If it is referred to 1 g of copper, the production rate is 28.88 g of 1,4-butynediol per gram of copper and per day.

EXAMPLE 2

The stainless steel autoclave of the Example 1 is charged with 300 mls of an aqueous solution of formaldehyde (9.3% by weight) and 74 mls (63 g) of the catalytic complex having a copper content of 2.77% by weight. By carrying out the reaction according to the conditions of Example 1, the following results are obtained:
(A) after 8 hours of reaction:
formaldehyde: 5.98%
1,4-butynediol: 4.25%
propargyl alcohol: 0.66%
(B) after 16 hours of reaction:
formaldehyde 4.12%
1,4-butynediol: 6.9%
propargyl alcohol: 0.66%
(C) after 29 hours of reaction:
formaldehyde: 1.0%
1,4-butynediol: 11.3%
propargyl alcohol: 0.77%

The production rate is 400 g of 1,4-butynediol per liter of catalyst and per day and, if referred to the copper by weight, is 17 g of 1,4-butynediol per gram of copper and per day.

EXAMPLE 3

In a stirred, heated and electrically thermostated reaction vessel, having a capacity of 4,500 Cu cm., there are charged 4,000 mls of a 30% formaldehyde aqueous solution, together with 132.6 g of catalytic complex having a copper content of 4.29%.

After the subsequent purging operations, by vacuum and nitrogen, carried out under cold conditions, both the heating system and the stirrer are switched on.

When the operating temperature of 90° C. is attained, acetylene, taken from a gas cylinder and suitably purified, is fed by bubbling through the reaction mixture at a pressure of 1.5 atm.

During the reaction the following data have been noted.

|  | after 12 hours | after 32 hours |
| --- | --- | --- |
| formaldehyde %: | 26 | 20 |
| 1,4-butynediol %: | 6.1 | 13.3 |
| propargyl alcohol %: | 1.19 | 1.19 |

The yield of 1,4-butynediol is 3,300 g/liter of catalyst per day and, if referred to 1 g of Cu is 78,23 g/1 Cu×24 h.

EXAMPLE 4

In a glass continuous reactor, with a fixed bed of catalyst, about 1,000 cu.cm. of the catalytic complex formed by 13×sodium zeolite, which was subject to ion exchange with copper up to 8,77% by weight, are changed on the catalyst supporting grid: the catalyst is in form of small spheres having 2 mm. diameter.

The reactor is then charged with 3.5. liters of a formaldeyde acqueous solution (35% by weight), and both the heating system (operating by oil circulation) and the oil circulation pump, as well as the plant circulation pumps are actuated.

A suitable pumping flow of nitrogen ensures the evacua-tion of the all the oxygen present in the system.

When the temperature is stabilized at 90° C., acetylene is fed from a cylinder gas (it being suitably purified) and the total pressure of the system is brought to 1.5 atm.

There are switched on the two operating pumps of the system, one for the feeding of formaldehyde and the other for the discharge of the reaction mixture and, after some hours, namely when the reactor is operating under steady conditions, the following data are noted:

formaldehyde: 20.17%
1,4-butynediol: 21.60%
propargyl alcohol: 1.30%

The production rate is 700 g of 1,4-butynediol per liter of catalytic complex and per day i.e. 28 g 1,4-butynediol/1 g Cu×24 h, if referred to the copper unit weight.

I claim:

1. A process for the preparation of 1,4-butynediol comprising reacting acetylene and formaldehyde at a temperature between 70° C. and 150° C. and at an acetylene pressure of between 0.5 and 1.5 atmospheres in the presence of a catalyst comprising an acetylide of copper supported on and chemically bonded to a molecular sieve material or a synthetic zeolite through an ion exchange reaction so that the copper atoms and the support form an inorganic, polymeric, crystal lattice in which the copper atoms are positioned at regularly distributed sites.

2. A process for the preparation of 1,4-butynediol according to claim 1, characterized in that said catalyst is brought into contact, in the reaction vessel, with acetylene in order to form the acetylide of copper, whereafter the true reaction is started.

3. A process as in claim 1, wherein the reaction is carried out at a temperature between 80° C. and 110° C.

* * * * *